United States Patent
Rault et al.

(10) Patent No.: US 6,875,788 B2
(45) Date of Patent: Apr. 5, 2005

(54) IMIDAZOLINE COMPOUNDS

(75) Inventors: Sylvain Rault, Moult (FR); Marina Kopp, Caen (FR); Jean-Charles Lancelot, Le Bourg (FR); Stéphane Lemaitre, Bois le Roi (FR); Daniel-Henri Caignard, Le Pecq (FR); Jean-Guy Bizot-Espiard, Paris (FR); Pierre Renard, Le Chesnay (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 10/689,394

(22) Filed: Oct. 20, 2003

(65) Prior Publication Data
US 2004/0087638 A1 May 6, 2004

(30) Foreign Application Priority Data
Oct. 23, 2002 (FR) ............................. 02 13194

(51) Int. Cl.⁷ .................. A61K 31/4164; C07D 233/04
(52) U.S. Cl. ..................... 514/397; 548/315.1
(58) Field of Search .................. 548/315.1; 514/397

(56) References Cited
U.S. PATENT DOCUMENTS 3,932,431 A * 1/1976 Walter ................. 546/275.1
4,081,544 A * 3/1978 Walter .................... 514/341
5,389,666 A * 2/1995 Hamanaka et al. ......... 514/400
6,093,727 A * 7/2000 Wong et al. ............... 514/299

* cited by examiner

*Primary Examiner*—Golam M M Shameem
(74) *Attorney, Agent, or Firm*—The Firm of Hueschen and Sage

(57) ABSTRACT

Compounds of formula (I):

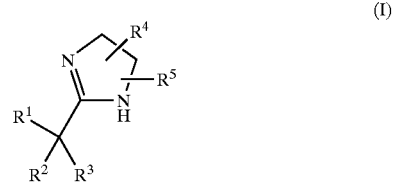

wherein:
$R^1$ represents an optionally substituted heteroaryl group,
$R^2$ represents an optionally substituted cycloalkyl group,
$R^3$ represents a hydrogen atom or an alkyl group, and
$R^4$ and $R^5$ are as defined in the description, and Medicinal products containing the same are useful in the treatment of non-insulin-dependent type II diabetes, obesity, type I diabetes, hyperlipidaemia, hypercholesterolaemia and cardiovascular complications thereof.

11 Claims, No Drawings

IMIDAZOLINE COMPOUNDS

SUMMARY OF THE INVENTION

The compounds of the present invention have a novel structure characterised by the combination of an imidazoline group and a cycloalkylimidazoline group that gives them antidiabetic properties without side effects owing to the absence of serotonin reuptake inhibition.

DESCRIPTION OF THE PRIOR ART

As far as chemical structures are concerned, the literature provides numerous examples of imidazoline compounds. They have been described, inter alia, for their therapeutic use. Imidazoline compounds are known, for example, to have cardiotonic properties (GB 119/963), α-adrenergic stimulating properties (Eur. J. Med. Chem., 1989, 24(6), 619, J. Pharmacobio. Dyn., 1986, 9(4), 395), antidepressant and anti-inflammatory properties (US 3932-431).

BACKGROUND OF THE INVENTION

Finally, other imidazoline derivatives have antihyperglycaemic and antidiabetic properties (EP 924 209, EP 1 145 717, EP 288 978, JP 04178381 and WO 02 38559) or to be capable of treating pathologies associated with imidazoline receptors (EP 846 688).

DETAILED DESCRIPTION OF THE INVENTION

The present invention relates to compounds of formula (I):

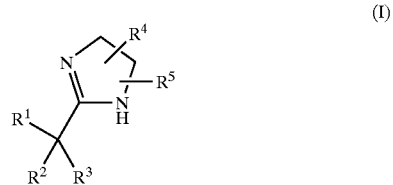

wherein
$R^1$ represents an optionally substituted heteroaryl group,
$R^2$ represents an optionally substituted cycloalkyl group,
$R^3$ represents a hydrogen atom or an alkyl group, and
$R^4$ and $R^5$, which may be identical or different, each represents a hydrogen atom, a halogen atom or an alkyl, polyhaloalkyl, $R^{10}$—C(X)—$R^{11}$—, $R^{10}$—Y—C(X)—$R^{11}$—, $R^{10}$—C(X)—Y—$R^{11}$—, $R^{10}$—Y—$R^{11}$— or $R^{10}$—S(O)$_n$—$R^{11}$— group,
in which:
$R^{10}$ represents a hydrogen atom or an alkyl group,
$R^{11}$ represents a bond, or an alkylene, alkenylene or alkynylene group,
X represents an oxygen atom, a sulphur atom, or an $NR^{12}$ group in which $R^{12}$ represents a hydrogen atom or an alkyl group,
Y represents an oxygen atom, a sulphur atom, or an amino or alkylamino group, and
n represents an integer of from 1 to 2 inclusive,
to their enantiomers, diastereoisomers, tautomers, and also addition salts thereof with a pharmaceutically acceptable acid or base,
it being understood that:
the term "alkyl" denotes a linear or branched hydrocarbon chain containing from 1 to 6 carbon atoms,
the term "alkoxy" denotes an alkyl-oxy group in which the alkyl chain, which may be linear or branched, contains from 1 to 6 carbon atoms,
the term "alkylene" denotes a linear or branched bivalent hydrocarbon chain containing from 1 to 6 carbon atoms,
the term "alkenylene" denotes a linear or branched bivalent hydrocarbon chain containing from 1 to 6 carbon atoms and from 1 to 3 double bonds,
the term "alkynylene" denotes a linear or branched bivalent hydrocarbon chain containing from 1 to 6 carbon atoms and from 1 to 3 triple bonds,
the term "polyhaloalkyl" denotes a linear or branched carbon chain containing from 1 to 3 carbon atoms and from 1 to 7 halogen atoms,
the term "heteroaryl" denotes a mono- or bi-cyclic group having from 5 to 11 ring members in which at least one of the rings is aromatic and containing in the monocycle or in the bicycle 1, 2 or 3 hetero atoms selected from nitrogen, oxygen and sulphur, and
the term "cycloalkyl" denotes a hydrocarbon monocycle or bicycle that contains from 3 to 10 carbon atoms and is optionally unsaturated by 1 or 2 unsaturated bonds;
the expression "optionally substituted" associated with the terms cycloalkyl and heteroaryl denotes that the groups in question are unsubstituted or substituted by one or two identical or different substituents selected from halogen atoms and the groups alkyl, alkoxy, hydroxy, cyano, nitro, amino (optionally substituted by one or two alkyl groups) and —C(O)$R_d$ wherein $R_d$ represents a group selected from hydroxy, alkoxy and amino, it being understood that the heteroaryl group may be additionally substituted by an oxo group on the non-aromatic moiety of the heteroaryl.

Among the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic and camphoric acid etc . . .

Among the pharmaceutically acceptable bases there may be mentioned, without implying any limitation, sodium hydroxide, potassium hydroxide, triethylamine, etc . . .

An advantageous aspect of the invention concerns compounds wherein $R^4$ and $R^5$, which may be identical or different, each represents a hydrogen atom or an alkyl group.

Another advantageous aspect concerns compounds of formula (I) wherein $R^3$ represents a hydrogen atom.

The preferred alkyl group of the invention for the groups $R^4$ and/or $R^5$ is the methyl group.

Preferred $R^2$ groups of the invention are the groups cyclopentyl, cyclohexyl and cycloheptyl, optionally substituted by an alkyl group, and more especially the cyclohexyl group.

Preferred heteroaryl groups of the invention are aromatic groups having 5 or 6 ring members, such as furyl, thienyl, pyrrolyl and pyridyl and, more especially, thienyl.

An especially advantageous aspect of the invention concerns compounds of formula (I) wherein $R^1$ represents a heteroaryl group having 5 or 6 optionally substituted ring members, $R^2$ represents a cyclohexyl or cycloheptyl group optionally substituted by an alkyl group, $R^3$ represents a hydrogen atom, and $R^4$ and $R^5$, which may be identical or different, each represents a hydrogen atom or an alkyl group.

Among the preferred compounds of the invention, the following may be mentioned more especially: 2-[cyclohexyl (3-thienyl)methyl]-4-methyl-4,5-dihydro-1H-imidazole and its tautomer 2-[cyclohexyl(3-thienyl)methyl]-5-methyl-4,5-dihydro-1H-imidazole, (4S)-2-[cyclohexyl (3-thienyl)methyl]-4-methyl-4,5-dihydro-1H-imidazole and its tautomer (4S)-2-[cyclohexyl (3-thienyl)methyl]-5-methyl-4,5-dihydro-1H-imidazole, (4R)-2-[cyclohexyl-(3-thienyl)methyl]-4-methyl-4,5-dihydro-1H-imidazole and its tautomer (4R)-2-[cyclohexyl (3-thienyl)methyl]-5-methyl-4,5-dihydro-1H-imidazole.

The invention relates also to a process for the preparation of compounds of formula (I), which is characterised in that there is used as starting material a compound of formula (II):

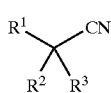

(II)

wherein $R^1$, $R^2$ and $R^3$ are as defined for formula (I), which compounds of formula (II) are condensed with a diamine (III):

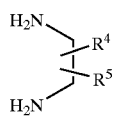

(III)

wherein $R^4$ and $R^5$ are as defined for formula (I) to yield, in the presence of an appropriate catalyst, compounds of formula (I), which may optionally be purified according to a conventional purification technique, which, if desired, are separated into their stereoisomers according to a conventional separation technique, which, if desired, are converted into additions salts with a pharmaceutically acceptable acid or base, it being understood that at any moment considered appropriate during the course of the process described above, the carbonyl, thiocarbonyl, amino or alkylamino group or groups of the starting reagents (II) and (III) may be protected and then, after condensation, deprotected for the purposes of the synthesis, the reagents (II) and (III) are prepared according to known procedures described in the literature.

The compounds exhibit, inter alia, excellent activity in reducing blood glucose levels. Those properties justify their therapeutic use in the treatment and/or prophylaxis of hyperglycaemia, dyslipidaemia and, more especially, in the treatment of non-insulin-dependent type II diabetes, obesity, glucose intolerance, and diabetic complications, especially in respect of the cardiovascular system.

The activity of the compounds is likewise recommended for the treatment and/or prophylaxis of other diseases, including type I diabetes, hypertriglyceridaemia, metabolic syndrome, insulin resistance, dyslipidaemia in diabetics, hyperlipidaemia and hypercholesterolaemia.

The compounds of the present invention in addition have a very weak affinity for serotonin receptor sites, and they are of low toxicity, unlike the prior art compounds.

The present invention relates also to pharmaceutical compositions comprising as active ingredient at least one compound of formula (I), on its own or in combination with one or more pharmaceutically acceptable, inert, non-toxic excipients or carriers.

Among the pharmaceutical compositions according to the invention there may be mentioned more especially those which are suitable for oral, parenteral or nasal administration, tablets or dragées, sublingual tablets, gelatin capsules, lozenges, suppositories, creams, ointments, dermal gels, etc.

The useful dosage varies in accordance with the age and weight of the patient, the nature and the severity of the disorder, and also the administration route, which may be oral, nasal, rectal or parenteral. Generally, the unit dosage ranges from 0.1 to 500 mg for a treatment of from 1 to 3 administrations per 24 hours.

The following Examples illustrate the invention and do not limit it in any way. The structures of the described compounds were confirmed by customary spectroscopic and spectrometric techniques.

The starting materials used are known products or products prepared according to known procedures.

The name of the example compounds hereinbelow also includes the tautomers thereof, for example 2-[cyclohexyl (3-thienyl)methyl]-4-methyl-4,5-dihydro-1H-imidazole and its tautomer 2-[cyclohexyl(3-thienyl)methyl]-5-methyl-4,5-dihydro-1H-imidazole.

GENERAL PROTOCOL A

Synthesis of Cycloalkylidene Acetonitrile Compounds (Preparations 1 to 6)

0.1 mol of acetonitrile compound is added to a solution of 0.1 mol of sodium ethanolate in 50 ml of ethanol, and then 0.1 mol of ketone compound is added. The mixture is heated at 60° C. for 4 hours, and the resulting solution is then concentrated under reduced pressure to half the initial volume and subsequently poured into 200 ml of water. Following extraction with ether, the ethereal fractions are washed with water and dried over magnesium sulphate and the solvent is evaporated off. The product so obtained will be used in the following step without additional purification.

GENERAL PROTOCOL B

Reduction of the Nitrogen-Containing Compounds (Preparations 7 to 12)

0.125 mol of sodium borohydride is added to a solution of 0.05 mol of compounds of Preparations 1–6 in 100 ml of ethanol. The solution is heated with reflux of ethanol for 24 hours and the ethanol is evaporated off under reduced pressure. The residue is taken up in 500 ml of water and extracted with ether. The desired product is obtained after drying the organic phase over magnesium sulphate and evaporating off the ether. The product so obtained will be used in the following step without additional purification.

Preparation 1

Cyclopentylidene(3-thienyl)acetonitrile

The expected intermediate is obtained in the manner described in General Protocol A starting from 3-thienylacetonitrile and cyclopentanone.

Preparation 2

Cyclohexylidene(2-thienyl)acetonitrile

The expected intermediate is obtained in the manner described in General Protocol A starting from 2-thienylacetonitrile and cyclohexanone.

Preparation 3

Cyclohexylidene(3-thienyl)acetonitrile

The expected intermediate is obtained in the manner described in General Protocol A starting from 3-thienylacetonitrile and cyclohexanone.

Preparation 4

(4-Methylcyclohexylidene)(3-thienyl)acetonitrile

The expected intermediate is obtained in the manner described in General Protocol A starting from 3-thienylacetonitrile and 4-methylcyclohexanone.

Preparation 5

Cycloheptylidene(3-thienyl)acetonitrile

The expected intermediate is obtained in the manner described in General Protocol A starting from 3-thienylacetonitrile and cycloheptanone.

Preparation 6

Cyclohexylidene(1-methyl-1H-pyrrol-2-yl)acetonitrile

The expected intermediate is obtained in the manner described in General Protocol A starting from (1-methyl-1H-pyrrol-3-yl)acetonitrile and cyclohexanone.

Preparation 7

Cyclopentyl(3-thienyl)acetonitrile

The expected intermediate is obtained in the manner described in General Protocol B starting from the compound of Preparation 1.

Preparation 8

Cyclohexyl(2-thienyl)acetonitrile

The expected intermediate is obtained in the manner described in General Protocol B starting from the compound of Preparation 2.

Preparation 9

Cyclohexyl(3-thienyl)acetonitrile

The expected intermediate is obtained in the manner described in General Protocol B starting from the compound of Preparation 3.

Preparation 10

(4-Methylcyclohexyl)(3-thienyl)acetonitrile

The expected intermediate is obtained in the manner described in General Protocol B starting from the compound of Preparation 4.

Preparation 11

Cycloheptyl(3-thienyl)acetonitrile

The expected intermediate is obtained in the manner described in General Protocol B starting from the compound of Preparation 5.

Preparation 12

Cyclohexyl(1-methyl-1H-pyrrol-2-yl)acetonitrile

The expected intermediate is obtained in the manner described in General Protocol B starting from the compound of Preparation 6.

Preparation 13

Cyclohexyl(pyrid-2-yl)acetonitrile 0.1 mol of 2-pyridylacetonitrile in 10 ml of benzene is added to a suspension of 0.011 mol of sodium amide in 15 ml of anhydrous benzene. The reaction mixture is heated at reflux for 3 hours. The solution is then allowed to return to ambient temperature in order to enable the dropwise addition of 0.1 mol of bromocyclohexane, and then the solution is again heated at reflux for 8 hours.

The mixture is cooled and 50 ml of water are added to eliminate the excess of sodium amide. The organic phase is extracted and dried over magnesium sulphate and the solvent is evaporated off under reduced pressure.

GENERAL PROTOCOL C

Synthesis of the Compounds of Examples 1 to 12

A catalytic amount of phosphorus pentasulphide (0.5 g, 0.001 mol) is added to 0.02 mol of the compounds of Preparations 7 to 13 in 25 ml of the chosen diamine compound. The mixture is heated at reflux for 5 hours. The solution is then poured into 50 ml of water and extracted twice with 50 ml of dichloromethane. Following evaporation of the solvent, the product is recrystallised from a minimum amount of acetonitrile.

EXAMPLE 1

2-[Cyclopentyl(3-thienyl)methyl]-4,5dihydro-1H-imidazole

The title compound is obtained according to General Protocol C starting from the compound of Preparation 7 and 1,2-ethanediamine.

Melting point: 157° C.

EXAMPLE 2

2-[Cyclohexyl(2-thienyl)methyl]-4,5-dihydro-1H-imidazole

The title compound is obtained according to General Protocol C starting from the compound of Preparation 8 and 1,2-ethanediamine.

Melting point: 155° C.

EXAMPLE 3

2-[Cyclohexyl(3-thienyl)methyl]-4,5-dihydro-1H-imidazole

The title compound is obtained according to General Protocol C starting from the compound of Preparation 9 and 1,2-ethanediamine.

Melting point: 182° C.

EXAMPLE 4

2-[Cyclohexyl(3-thienyl)methyl]-4,5-dihydro-1H-imidazole, enantiomer 1

By separating the compound described above in Example 3 by chiral chromatography, one of the enantiomers is isolated.

EXAMPLE 5

2-[Cyclohexyl(3-thienyl)methyl]-4,5-dihydro-1H-imidazole, enantiomer 2

By separating the compound described above in Example 3 by chiral chromatography, the other enantiomer is isolated.

EXAMPLE 6

2-[Cyclohexyl(3-thienyl)methyl]-4-methyl-4,5dihydro-1H-imidazole

The title compound is obtained according to General Protocol C starting from the compound of Preparation 9 and 1,2-propanediamine.

Melting point: 155° C.

EXAMPLE 7

2-[Cyclohexyl(3-thienyl)methyl]-4,4-dimethyl-4,5-dihydro-1H-imidazole

The title compound is obtained according to General Protocol C starting from the compound of Preparation 9 and 2-methyl-1,2-propanediamine.

Melting point: 162° C.

EXAMPLE 8

2-[(4-Methylcyclohexyl)(3-thienyl)methyl]-4,5-dihydro-1H-imidazole

The title compound is obtained according to General Protocol C starting from the compound of Preparation 10 and 1,2-ethanediamine.

Melting point: 168° C.

EXAMPLE 9

2-[Cyclohexyl(1-methyl-1H-pyrrol-2-yl)methyl]-4,5-dihydro-1H-imidazole

The title compound is obtained according to General Protocol C starting from the compound of Preparation 12 and 1,2-ethanediamine.

Melting point: 120° C.

EXAMPLE 10

2-[Cyclohexyl(4,5dihydro-1H-imidazol-2-yl)methyl]pyridine

The title compound is obtained according to General Protocol C starting from the compound of Preparation 13 and 1,2-ethanediamine.

Melting point: 116° C.

EXAMPLE 11

2-[Cycloheptyl(3-thienyl)methyl]-4,5-dihydro-1H-imidazole

The title compound is obtained according to General Protocol C starting from the compound of Preparation 11 and 1,2-ethanediamine.

Melting point: 155° C.

EXAMPLE 12

2-[Cycloheptyl(3-thienyl)methyl]-4-methyl-4,5-dihydro-1H-imidazole

The title compound is obtained according to General Protocol C starting from the compound of Preparation 11 and 1,2-propanediamine.

Melting point: 125° C.

EXAMPLE 13

(4S)-2-[Cyclohexyl(3-thienyl)methyl]-4methyl-4,5-dihydro-1H-imidazole

The title compound is obtained according to General Protocol C starting from the compound of Preparation 9 and (2S)-1,2-propanediamine.

Melting point: 153° C.

EXAMPLE 14

(4R)-2-[Cyclohexyl(3-thienyl)methyl]-4-methyl-4,5-dihydro-1H-imidazole

The title compound is obtained according to General Protocol C starting from the compound of Preparation 9 and (2R)-1,2-propanediamine.

Melting point: 154° C.

PHARMACOLOGICAL STUDY

EXAMPLE A

Hypoglycaemic Activity

The hypoglycaemic activity of the compounds of the invention was examined in three-month-old male Wistar rats weighing about 250 g. An experimental diabetes is obtained by the iv injection, under ketamine hydrochloride anaesthesia, of a low dose of streptozotocin (35 mg/kg iv) dissolved in a citrate buffer. Such rats are called STZ rats and are characterised by a slight basal hyperglycaemia, a marked intolerance to glucose and a clear change in the secretion of insulin.

Homeostasis was evaluated by a glucose tolerance test, carried out two weeks after injection with streptozotocin.

Finally, the hypoglycaemic activity was evaluated in "Zucker" rats. "Zucker fatty" fa/fa rats arose following a spontaneous mutation of the 13M strain (Zucker & Zucker, 1961), and are genetically insulin-resistant and obese.

Their obesity can be observed from the age of four weeks, and is thus accompanied by insulin resistance, hyperinsulinaemia and hyperlipidaemia. This model is predictive of diabetic conditions exhibiting associated metabolic disorders, such as obesity. Homeostasis was evaluated likewise by a glucose tolerance test.

Oral Glucose Tolerance Test (OGTT)

Glucose is administered per os (2 g/kg) to conscious rats. Blood samples are collected before and 10, 20, 30, 40, 60, 90 and 120 minutes after the glucose administration.

The product to be tested is administered per os 1 hour before the OGTT, and the control animals receive solvent (gum arabic).

The compounds of the invention reduce glycaemia very significantly.

For example, at 10 mg/kg, the compound of Example 6 reduces glycaemia by 13%, 18% and 14% in non-diabetic Wistar rats, STZ Wistar rats and Zucker rats, respectively.

EXAMPLE B

Hypolipaemic Activity

The products of the invention were tested in vivo in the obese ob/ob mouse, used as a model of obesity-associated insulin resistance. By way of example, the compound of Example 6 significantly lowers the triglycerides (after chronic administration by the oral route at a dose of 30 mg/kg/day for 4 days) by 32% (animals treated with the compound of Example 6 vs. untreated animals). In this model, the compounds of the invention are thus shown also to be powerful hypolipaemics.

EXAMPLE C

Determination of the Affinity for Serotonin Reuptake Sites in the Rat

The affinity of the compounds of the invention was determined by competition experiments with [$^3$H]- paroxetine. The membranes from the rat frontal cortex are prepared and incubated in triplicate for 2 hours, at 25° C., with 0.25 nM [$^3$H]-paroxetine and the cold ligand in a final volume of 0.4 ml. The incubation buffer contains 50 mM TRIS-HCl (pH 7.4), 120 mM NaCl and 5 mM KCl. The non-specific binding is determined using 10 μM citalopram. At the end of incubation, the medium is filtered through filters and washed three times with 5 ml of cooled buffer. The radioactivity retained on the filters is determined by liquid scintillation counting. The binding isotherms are analysed by non-linear regression in order to determine the $IC_{50}$ values.

It appears that the compounds of the invention exhibit a weaker affinity for the serotonin reuptake sites than the compounds of the prior art, and thus a decrease in central toxicity confirmed by the Irwin test (see Example D).

By way of example, the compound of Example 3 has an $IC_{50}$ of $2\times10^{-6}$M, which is superior to that of the prior art (EP 846 688): 2-[cyclohexyl(phenyl)methyl]-4,5-dihydro-1H-imidazole ($1.5\times10^{-7}$ M).

EXAMPLE D

Acute Toxicity Study—Irwin Test

Three rats per dose are treated per os with one of the compounds of the invention (dispersed in 0.5% carboxymethyl cellulose in distilled water) and are observed at regular intervals after 24 hours. The presence or absence of the following symptoms are recorded: mortality, sedation, excitation, aggressiveness, tail form, convulsions, pain, trembling, exophthalmia, salivation, piloerection, defecation, fear, etc, according to the criteria described by Irwin (Psychopharmacologia, 1968, 13, 222). This test enables the toxicity and the effect on behaviour to be evaluated.

It appears that the compounds of the invention, according to the therapeutic index (ratio of the minimum active dose to the dose at which symptoms appear in the central nervous system), are less toxic than those of the prior art.

EXAMPLE E

Pharmaceutical Composition

Formulation for the preparation of 1000 tablets each containing a dose of 10 mg:

| | |
|---|---:|
| compound of Example 6 | 10 g |
| hydroxypropyl cellulose | 2 g |
| wheat starch | 10 g |
| lactose | 100 g |
| magnesium stearate | 3 g |
| talc | 3 g |

What is claimed is:
1. A compound selected from those of formula (I):

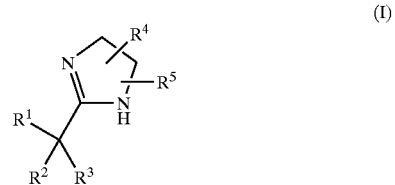

(I)

wherein:
$R^1$ represents an optionally substituted 5-membered heteroaryl group,
$R^2$ represents an optionally substituted cycloalkyl group,
$R^3$ represents a hydrogen atom or an alkyl group, and
$R^4$ and $R^5$, which may be identical or different, each represents a hydrogen atom, a halogen atom, an alkyl, group or a polyhaloalkyl group,
its enantiomers, diastereoisomers and tautomers thereof, and also addition salts thereof with a pharmaceutically acceptable acid or base.

2. A compound of claim 1 wherein $R^4$ and $R^5$, which may be identical or different, each represents a hydrogen atom or an alkyl group.

3. A compound of claim 1 wherein $R^3$ represents a hydrogen atom.

4. A compound of claim 1 wherein $R^2$ represents a cyclopentyl, cyclohexyl or cycloheptyl group optionally substituted by an alkyl group.

5. A compound of claim 1 wherein $R^1$ represents an optionally substituted 5-membered heteroaryl group, $R^2$ represents a cyclohexyl or cycloheptyl group optionally substituted by an alkyl group, $R^3$ represents a hydrogen atom and $R^4$ and $R^5$, which may be identical or different, each represents a hydrogen atom or an alkyl group.

6. A compound of claim 1 wherein the alkyl group is a methyl group.

7. A compound of claim 1 which is 2-[cyclohexyl(3-thienyl)methyl]-4-methyl-4,5-dihydro-1H-imidazole, its enantiomers, diastereoisomers and tautomers thereof, and also addition salts thereof with a pharmaceutically acceptable acid.

8. A compound of claim 1 which is (4S)-2-[cyclohexyl(3-thienyl)methyl]-4-methyl-4,5-dihydro-1H-imidazole, its diastereoisomers and tautomers thereof, and also addition salts thereof with a pharmaceutically acceptable acid.

9. A compound of claim 1 which is (4R)-2-[cyclohexyl(3-thienyl)methyl]-4-methyl-4,5-dihydro-1H-imidazole, its diastereoisomers and tautomers thereof, and also addition salts thereof with a pharmaceutically acceptable acid.

10. A pharmaceutical composition comprising as active principle an effective amount of a compound of claim 1 together with one or more pharmaceutically-acceptable excipients or vehicles.

11. A method for treating a living animal body afflicted with a pathology associated with non-insulin-dependent type II diabetes, obesity, and type I diabetes, thereof, comprising the step of administering to the living body an amount of a compound of claim 1 which is effective for alleviation of the pathology.

* * * * *